United States Patent
Inakagata et al.

[19]

[11] Patent Number: 5,928,505
[45] Date of Patent: Jul. 27, 1999

[54] DEVICE FOR PURIFYING AND DISPENSING WATER

[75] Inventors: Satoru Inakagata, Nara; Takahiro Heiuchi, Osaka, both of Japan

[73] Assignee: Matsushita Electric Works, Ltd., Osaka, Japan

[21] Appl. No.: 08/979,788

[22] Filed: Nov. 26, 1997

[30] Foreign Application Priority Data

Nov. 26, 1996 [JP] Japan ...................................... 8-314364

[51] Int. Cl.$^6$ .............................. B01D 17/12; C25B 9/04; H02J 7/12; A61C 17/00
[52] U.S. Cl. ......................... 210/91; 204/228.1; 204/271; 204/273; 204/274; 210/138; 210/188; 210/243; 320/108; 320/125; 422/186.04; 433/80; 433/82; 601/162
[58] Field of Search .................................. 433/80, 82, 85, 433/86, 87, 88, 84; 601/162; 210/86.91, 143, 149, 243, 188; 422/186.04; 204/228.1, 228.2, 229.2, 229.4, 242, 271, 273, 274; 320/103, 108, 137, 138, 150, 125, 126, DIG. 28–30; 363/18

[56] References Cited

U.S. PATENT DOCUMENTS

| | | |
|---|---|---|
| 3,996,126 | 12/1976 | Rasmussen .............................. 204/271 |
| 4,422,032 | 12/1983 | Kakumoto et al. .............. 320/DIG. 28 |
| 4,502,001 | 2/1985 | Galloway . |
| 4,551,666 | 11/1985 | Wada et al. ....................... 320/DIG. 28 |
| 4,755,735 | 7/1988 | Inakagata . |
| 5,371,454 | 12/1994 | Marek . |
| 5,493,747 | 2/1996 | Inakagata et al. . |
| 5,550,452 | 8/1996 | Shirai et al. . |
| 5,634,791 | 6/1997 | Matsuura et al. .......................... 433/87 |
| 5,680,028 | 10/1997 | McEachern ............................. 320/108 |
| 5,706,183 | 1/1998 | Abe et al. . |

FOREIGN PATENT DOCUMENTS

| | | |
|---|---|---|
| 63-286148 | 11/1988 | Japan . |
| 4306452 | 10/1992 | Japan . |
| 5-76550 | 3/1993 | Japan . |

*Primary Examiner*—Joseph W. Drodge
*Attorney, Agent, or Firm*—Greenblum & Bernstein, P.L.C.

[57] ABSTRACT

The present invention is directed to a water purification and dispensing apparatus which receives power through induction to eliminate the presence of exposed electrical contacts terminals. The water dispenser includes a motor driven pump, a water storage area, a rechargeable battery and a nozzle, such that water is pumped from the water storage area out through the nozzle. Two electrodes are provided in either the water storage area or a separate tank for purifying water placed therein. When the dispenser and/or purifying tank is mounted on a base, inductors in the base, the dispenser, and the tank connect via mutual inductance such that power supplied by the base is received by the dispenser and tank. Since power transfers magnetically, there are no exposed contact points which could corrode and/or short if water is accidentally spilled thereon.

38 Claims, 16 Drawing Sheets

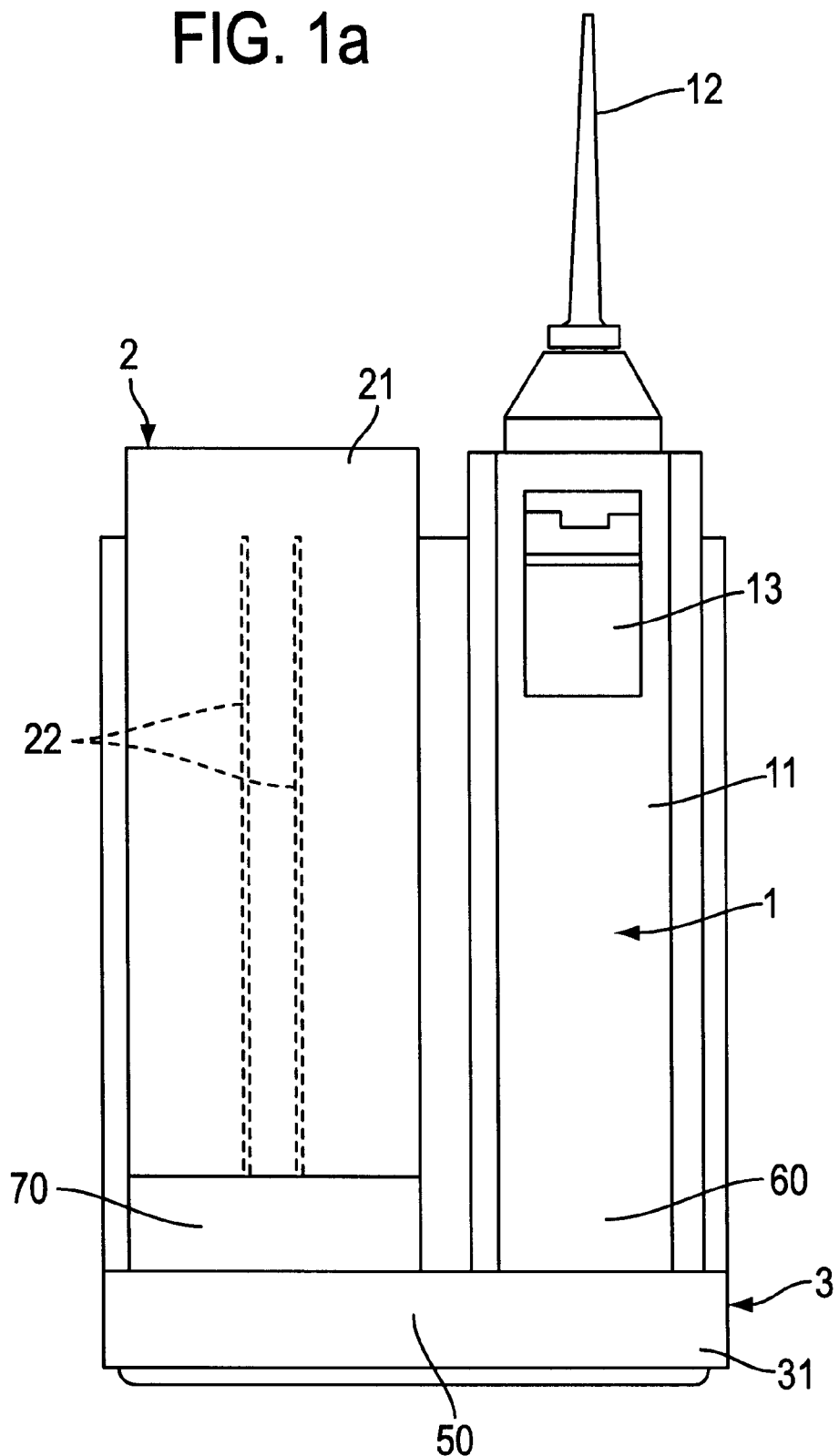

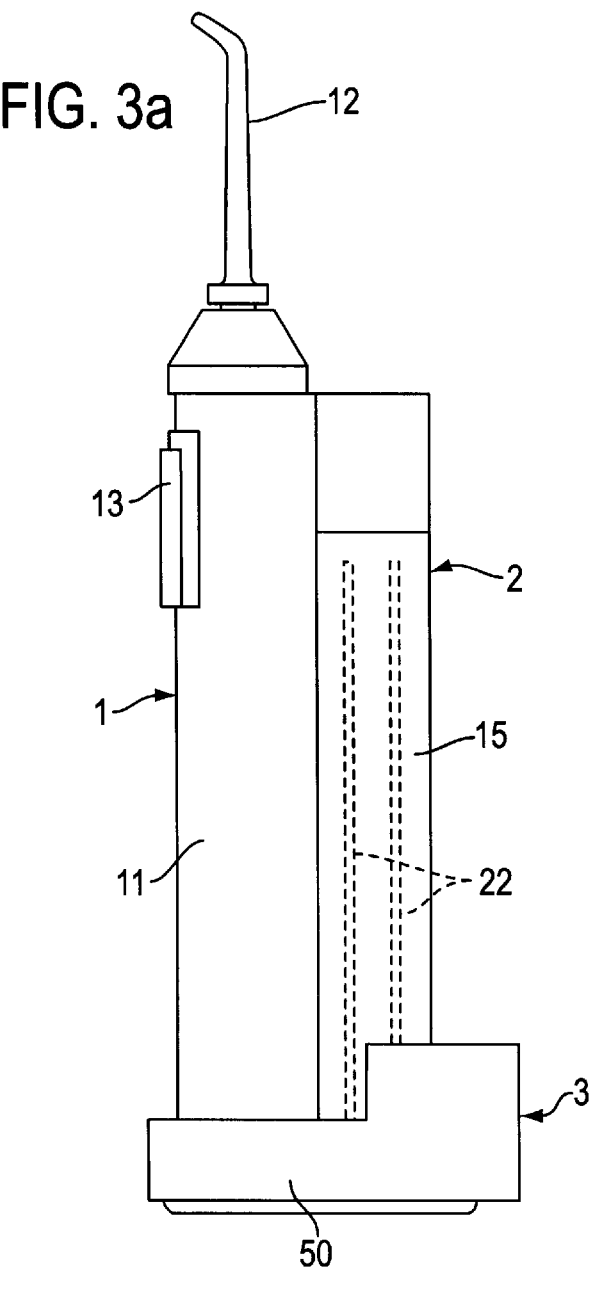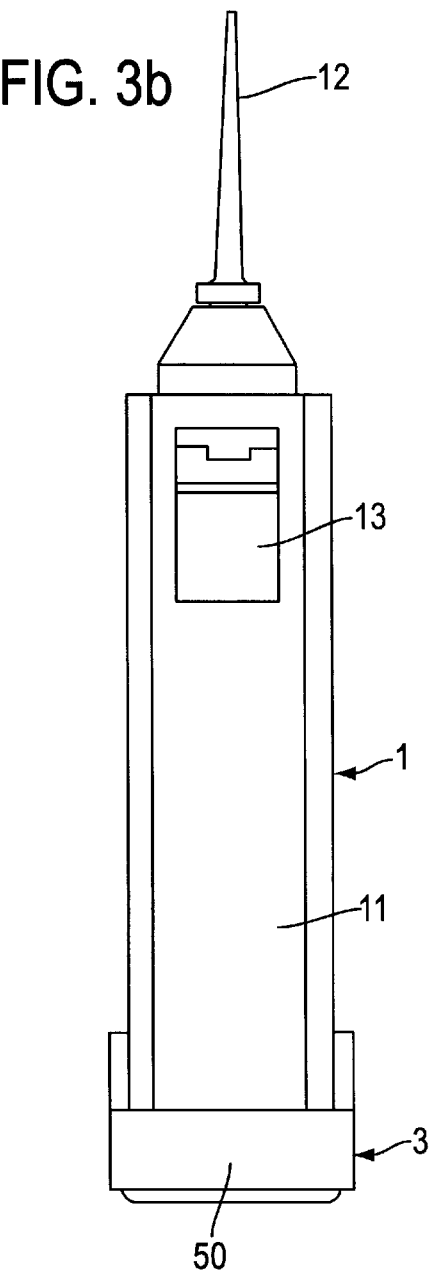

5,928,505

DEVICE FOR PURIFYING AND DISPENSING WATER

BACKGROUND OF THE INVENTION

1. Field of the Invention

The present invention is related to a water purifier and dispenser. More specifically, the present invention is directed to a device that purifies water by applying a current thereto, and dispenses such water for hygiene purposes, such as washing teeth or eyes.

2. Background and Material Information

In a typical prior art water purifier and dispenser, shown for example in Japanese Unexamined Patent Application HEI 5-76550, electrodes in a tank purify water therein through electrolysis, i.e., passing current between two electrodes. A pump beneath the tank transferred water in the tank out through a nozzle tethered to the device by a flexible hose. This prior art device was limited in its versatility due to the need to plug the device into a wall outlet to power the water dispenser. In combination with the limited length of the hose, the range of use of the prior art device is quite limited.

In response to the above drawback, the assignee of the present application developed a portable water dispensing device, shown in copending application 08/490,148, now U.S. Pat. No. 5,634,791. This device has an independent water storage area for holding water. Since the device is not tethered to the water purification tank, the length of hose does not limit the user between the dispenser and the tank of the prior art. Further, the device may be powered inductively (i.e., an inductor in a power source causes an inductor in the dispenser to generate current), such that there are no metal contacts that can short or corrode if water spills thereon. Since they require no direct electrical contact, the dispenser and the base can both be made waterproof, thereby eliminating concerns of corrosion and electric shock.

A drawback of the above prior art is that the purifier remains tethered to the wall outlet to receive power. Thus, the user must continuously return to the site of the purifying tank to refill the dispenser water storage area as needed.

SUMMARY OF THE INVENTION

It is accordingly an object of the present invention to overcome the drawbacks of the prior art.

Another object of the present invention is to provide a device that powers both a water purification section and a water dispensing section inductively to eliminate exposed terminals, and therefore does not suffer from corroding terminals due to exposure to the environment and/or the acidic purified water.

It is another object of the invention to provide a portable unit in which both the dispenser and purifier are not tethered to any power source, and may be repositioned at a user's convenience.

According to the above objects of the invention, there is provided a device for purifying and dispensing a fluid. A dispenser includes a fluid storage area, a pump that pumps fluid from the fluid storage area, and a first power receiving circuit having a first rechargeable battery for powering the pump. A purifying tank includes a fluid purification area having a pair of electrodes and a second power receiving circuit connected to the pair of electrodes. The first and second power receiving circuits include at least first and second inductors, respectively. A base unit has a power supply circuit including at least third and fourth inductors. The dispenser and the purifying tank are removably mounted on the base such that the first and third inductors and the second and fourth inductors are in sufficient proximity to each other to form mutual inductance therebetween when the dispenser and the purification tank are mounted on the base, respectively, such that current passing through the third inductor induces current in the first inductor, and current passing through the fourth inductor induces current in the second inductor.

According to a feature of the above embodiment, a variable switch changes an operating speed of the pump.

According to another feature of the above embodiment, a stirrer member stirs fluid in the purifying tank. The stirrer can be positioned at a bottom of the purifying tank. The stirrer is preferably inactive when voltage is applied to the pair of electrodes.

According to another feature of the above embodiment, a temperature adjusting element is associated with the purifying tank to at least one of increase and decrease a temperature of a fluid in the purifying tank.

According to yet another feature of the above embodiment the second power receiving circuit includes a timer circuit that controls the period of time that voltage is applied to the pair of electrodes.

According to still yet another feature of the above embodiment, the second power receiving circuit includes a constant current circuit for providing a constant current to the pair of electrodes. A variable switch may adjust an amount of current produced by the constant current circuit.

According to another feature of the above embodiment, the second power receiving circuit includes a switching circuit that changes a direction of current flow between the pair of electrodes. The switching circuit preferably only changes the direction of current flow once during a purification cycle. The switching circuit also preferably gradually decreases the current before changing the direction of current flow, and then gradually increases the current after changing the direction of current flow.

According to yet another feature of the above embodiment, the first power receiving circuit receives power through mutual inductance between the first and third inductors to apply voltage to charge the first rechargeable battery.

According to yet another feature of the above embodiment, the second power receiving circuit receives power through mutual inductance between the second and fourth inductors to apply voltage to the pair of electrodes.

According to still yet another feature of the above embodiment, the second power receiving circuit receives power through mutual inductance between the second and fourth inductors to charge a second rechargeable battery in the second power circuit. The second battery applies voltage to the pair of electrodes through a switch.

According to still yet another feature of the above embodiment, the first power source includes a mechanism that prevents the application of voltage to the pair of electrodes when the purifying tank does not have enough fluid to create a current path between the pair of electrodes.

According to yet another feature of the above embodiment, the purifying tank has a lid with a catalyst that absorbs gases produced during purification of the fluid, and an opening to expel the gases.

According to still yet another feature of the above embodiment, the purification tank has a pivoted lid and a switch associated with the lid that prevents current from flowing to the electrodes when the lid is open.

According to still yet another feature of the above embodiment, the power supplying circuit includes a circuit which minimizes a current flow through the first and second inductors when the purification tank is not mounted on the base, and which increases the current flow through the first and second inductors when the purification tank is mounted on the base.

According to another embodiment of the invention, there is provided a device for purifying and dispensing a fluid. A dispenser includes a fluid purification area, a pump which pumps fluid from the fluid storage area, and a first power receiving circuit having first rechargeable battery for powering the pump. The fluid purification area has a pair of electrodes and a second power receiving circuit connected to the pair of electrodes. The first and second power receiving circuits include at least first and second inductors, respectively. A base unit has a power supply circuit including at least third and fourth inductors. The dispenser is removably mounted on the base such that the first and third inductors and second and fourth inductors are in sufficient proximity to each other to form mutual inductance therebetween when the dispenser is mounted on the base, such that the current passing through the third inductor induces current in the first inductor, and current passing through the fourth inductor induces current in the second inductor.

According to a feature of the above embodiment, a variable switch changes an operating speed of the pump.

According to another feature of the above embodiment, a stirrer member stirs fluid in the purifying tank. The stirrer can be positioned at a bottom of the purifying tank. The stirrer is preferably inactive when voltage is applied to the pair of electrodes.

According to another feature of the above embodiment, a temperature adjusting element is associated with the purifying tank to at least one of increase and decrease a temperature of a fluid in the purifying tank.

According to yet another feature of the above embodiment, the second power receiving circuit includes a timer circuit which controls the period of time that voltage is applied to the pair of electrodes.

According to still yet another feature of the above embodiment, the second power receiving circuit includes a constant current circuit for providing a constant current to the pair of electrodes. A variable switch may adjust an amount of current produced by the constant current circuit.

According to another feature of the above embodiment, the second power receiving circuit includes a switching circuit which changes a direction of current flow between the pair of electrodes. The switching circuit preferably only changes the direction of current flow once during a purification cycle. The switching circuit also preferably gradually decreases the current before changing the direction of current flow, and then gradually increases the current after changing the direction of current flow.

According to yet another feature of the above embodiment, the first power receiving circuit receives power through mutual inductance between the first and third inductors to apply voltage to charge the first rechargeable battery.

According to yet another feature of the above embodiment, the second power receiving circuit receives power through mutual inductance between the second and fourth inductors to apply voltage to the pair of electrodes.

According to still yet another feature of the above embodiment, the second power receiving circuit receives power through mutual inductance between the second and fourth inductors to charge a second rechargeable battery in the second power circuit. The second battery applies voltage to the pair of electrodes through a switch.

According to still yet another feature of the above embodiment, the first power source includes a mechanism which prevents the application of voltage to the pair of electrodes when the purifying tank does not have enough fluid to create a current path between the pair of electrodes.

According to yet another feature of the above embodiment, the purifying tank has a lid with a catalyst which absorbs gases produced during purification of the fluid, and an opening to expel the gases.

According to still yet another feature of the above embodiment, the purification tank has a pivoted lid and a switch associated with the lid which prevents current from flowing to the electrodes when the lid is open.

According to still yet another feature of the above embodiment, the power supplying circuit includes a circuit which minimizes a current flow through the first and second inductors when the purification tank is not mounted on the base, and which increases the current flow through the first and second inductors when the purification tank is mounted on the base.

BRIEF DESCRIPTION OF THE DRAWINGS

FIGS. 1a and 1b are front and side views of a first embodiment of a water purifying and dispensing device according to the present invention.

FIGS. 3a and 3b are front and side views of a second embodiment of a water purifying and dispensing device according to the present invention.

DETAILED DESCRIPTION OF THE PREFERRED EMBODIMENTS

Figure 1B:
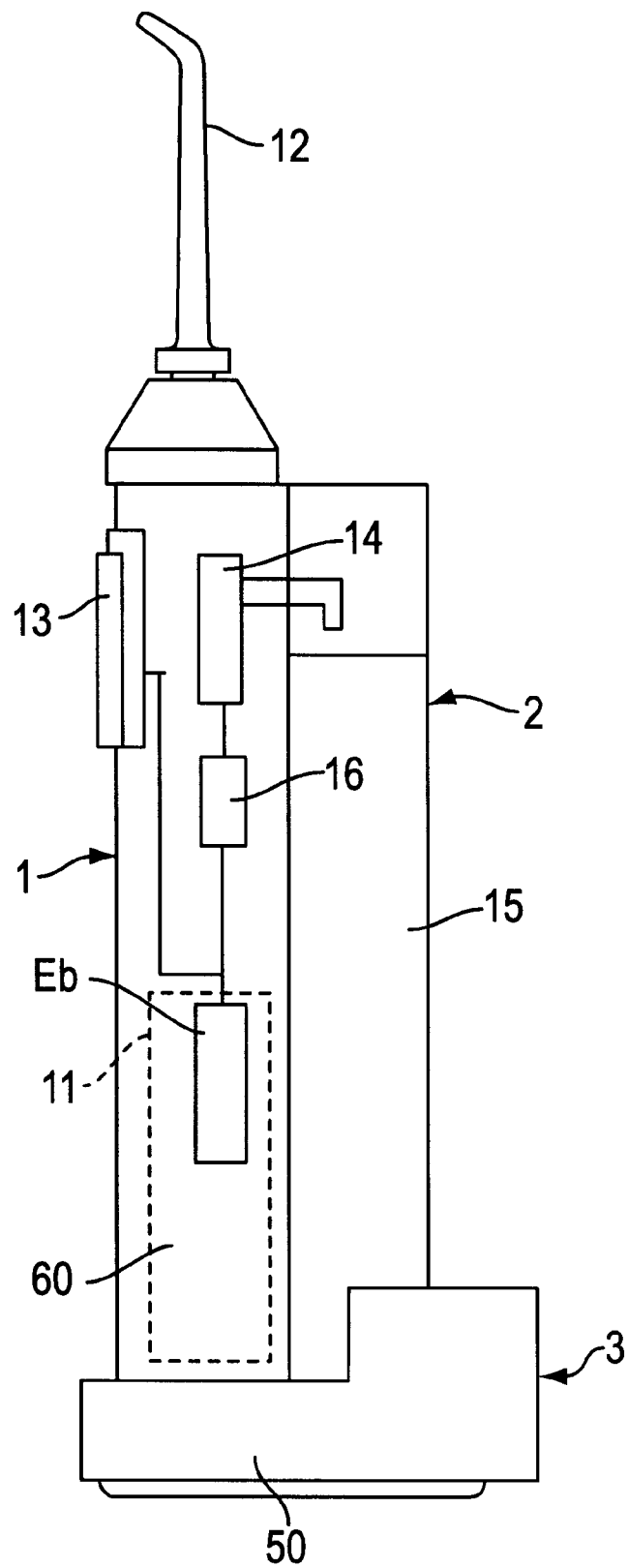

A first embodiment of the invention is shown in FIGS. 1a and 1b. The device includes a washer 1, and a purifier 2 supported on a housing 31 of a base 3. Washer 1 and purifier 2 are removably mounted to base 3, and may be individually removed at a user's discretion.

Washer 1 includes a housing 11, a nozzle 12 attached at an end thereof, and a control switch 13. Housing 11 supports a pump 14, a water storage area 15, a motor 16 which drives pump 14, and a power receiving circuit 60. Power receiving circuit 60 energizes motor 16 to operate pump 14 under control from an ON-OFF control switch 13. Water in water storage area 15 ejects through nozzle 12 under pressure from pump 14. Although these elements are well known in the art, a detailed description of a preferred mechanical configuration is disclosed in copending application U.S. Ser. No. 08/490,148, now U.S. Pat. No. 5,634,791 which is expressly incorporated herein by reference in its entirety. However, the invention is not limited to this structure, and may use any configuration of the elements as may be required.

Purifier 2 includes a tank 21 having electrodes 22 therein. Electrodes 22 connect to a power source 70 placed below tank 21. When tank 21 is filled with tap water, the application of DC current between electrodes 22 produces a small amount of hypochlorous acid, converting the tap water into an acidic purified solution (purified water). A user then pours the purified water as needed into water storage area 15 of washer 1 for later use.

Washer 1 and purifier 2 are mounted removably and separately to a base 3. A user can therefore remove and manipulate washer 1 without being tethered to tank 21; when cleaning a person's mouth to remove debris or bacteria, this improved versatility of this device makes it much easier to disperse purified water as needed. Similarly, the user can remove purifier 2 and place it in a suitable position to refill washer 1 as need.

Figure 2:
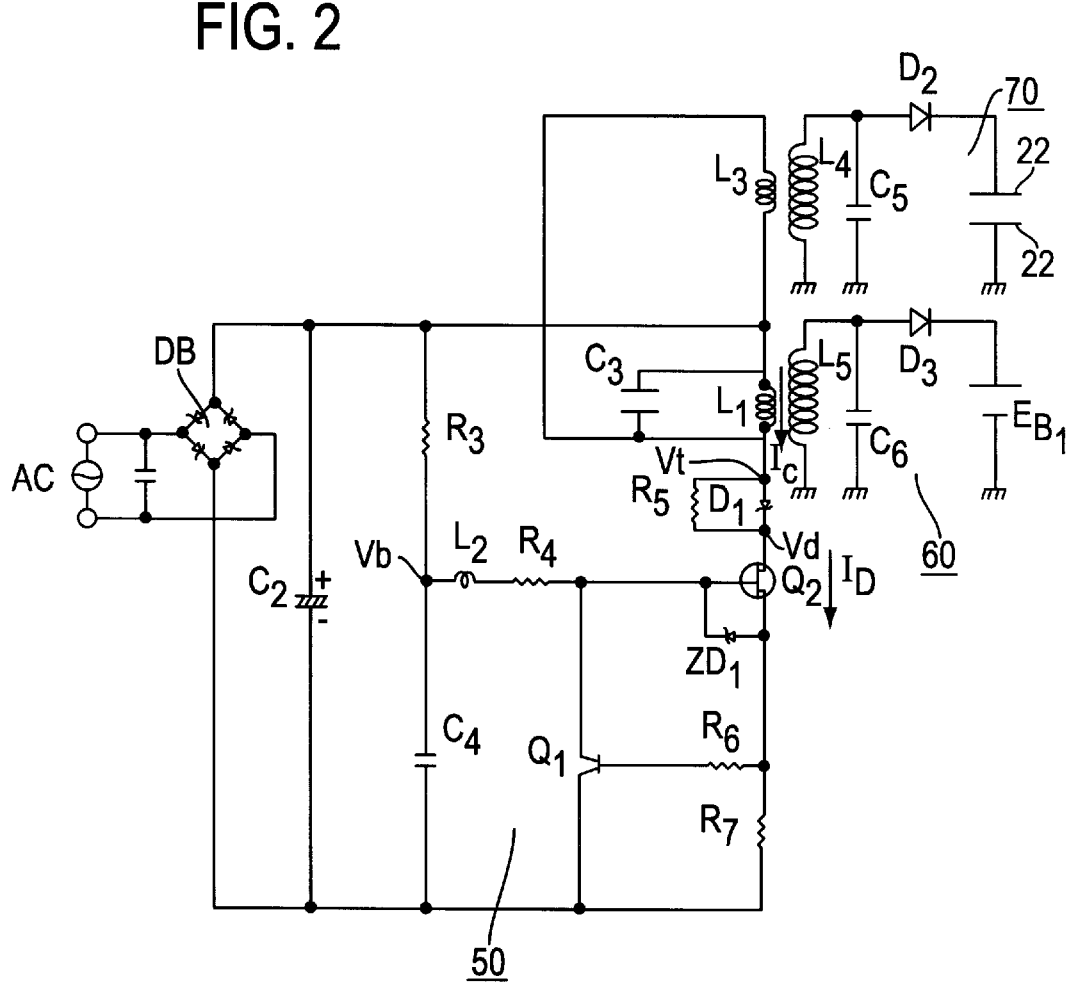
FIG. 2 is a schematic of a first circuit for powering the water purifying section and the dispenser according to the present invention.

Referring now to FIG. 2, base 3 includes a power supply circuit 50 which plugs into a standard outlet to supply power to power receiving circuits 60 and 70, respectively. Circuit 50 includes a diode bridge DB and a capacitor C2 to rectify and smooth current from current source AC. When connected to an AC power source, a capacitor C4 charges through resistor R3. A voltage Vb, input to a gate of a field effect transistor Q2 through a feedback inductor L2 and resistor R4, increases as capacitor C4 charges. Transistor Q2 begins to turn ON when voltage Vb increases beyond the threshold voltage of transistor Q2, such that a current ID may pass through the drain/source of transistor Q2. Current initially flows to charge capacitor C3, and then through the parallel inductance formed by inductors L1 and L3. Eventually, current IL through inductors L1 and L3 matches a current ID through transistor Q2.

Although not spatially reflected by the schematic of circuit 50, inductors L1 and L2 are in mutual inductance such that current IL through inductor L1 generates voltage across inductor L2. The resultant increase in voltage at the gate of transistor Q2 turns it fully ON, increasing current ID. The voltage produced by current ID through resistor R7 is applied to the gate of a transistor Q1 through resistor R6. When ID approaches its maximum, the voltage ($ID_{max} \cdot R_7$) crosses the threshold voltage of the gate of transistor Q1. Transistor Q1 turns ON, creating a path from capacitor C4 to ground through inductor L2, resistor R4, and transistor Q1.

As capacitor C4 discharges through this current path, voltage Vb drops, beginning to turn transistor Q2 OFF. The corresponding drop in current ID and current IL reduces the feedback voltage across inductor L2. This further lowers voltage Vb below the threshold level of transistor Q2, turning it completely OFF. The break in current ID also shuts transistor Q1 completely OFF.

When transistor Q2 is ON, current ID builds up energy in capacitor C3 and inductors L1 and L3. When transistor Q2 turns OFF, capacitor C3 and inductors L1 and L3 are in a state of free oscillation, i.e., capacitor C3 creates an oscillating current in inductors L1 and L3.

The oscillating current through inductor L1 generates a corresponding oscillating current in inductor L5 of power receiving circuit 60. Power receiving circuit 60 also includes a capacitor C6, a diode D3, and a rechargeable battery EB1 (which may be a Ni-CD battery). Capacitor C6 acts as a filter, while inductor L5 and diode D3 form a rectifier. These components convert oscillating current generated in inductor L5 into a DC current which charges battery EB1.

Similarly, the oscillating current in inductor L3 generates a corresponding current in inductor L4 of power receiving circuit 70. Power receiving circuit 70 also includes a capacitor C5, a diode D2, and electrodes 22. Capacitor C5 acts as a filter, while inductor L4 and diode D3 form a rectifier. These components convert the oscillating current generated in inductor L4 to provide a DC current to electrodes 22, purifying any water in tank 21.

The energy resonating through capacitor C3 and inductors L1 and L2 decreases due to the above power transfer to inductors L4 and L5, as well as some loss to heat. However, due to the mutual inductance between inductors L1 and L2, the resonance through inductor L1 generates a feedback voltage in inductor L2. In accordance with the waveform of current IL through inductor L1, voltage Vb rises to begin to turn transistor Q2 ON again.

With transistor Q2 beginning to return to the ON state, the above cycle repeats as described above to resupply energy to capacitor C3 and inductors L1 and L2. The circuit reaches stable oscillation when voltage Vb of capacitor C4 reaches an equilibrium state through charging by resistor R3 and discharging through transistor Q1.

Since power transfers inductively from power supply circuit 50 to power receiving circuits 60 and 70, there is no physical electrical contact between washer 1, purifier 2 and base 3, i.e., there are no exposed metallic terminals. Absent such electric contacts, the present invention will not experience any problems associated with corrosion of the contacts, the collection of debris therein, and/or cleaning or replacing contacts. In addition, since no electrical terminals are exposed, spilled water will not short circuit the device.

In the above embodiment, washer 1 and purifier 2 are separate elements. A user therefore simply pours purified water into storage tank 15 of washer 1 through an appropriate opening in housing 11 as needed.

Referring now to FIGS. 3a and 3b, a second embodiment of the invention combines the washer 1 and purifier 2 into an integral hand-held unit by connecting electrodes 22 in water storage area 15. Water storage area 15 thus purifies the water and stores the same for washer 1 to dispense. The remaining elements of this embodiment are the same as the first embodiment, save that (1) power receiving area 70 is below electrodes 22 in water storage area 15, and (2) the elements of power supply circuit 50 are physically arranged to comport with the new position of electrodes 22.

The above integrated design reduces the overall size and weight of washer 1 compared with the washer 1 and purifier 2 of FIGS. 1a and 1b, making it more convenient as a portable model. Although water storage area 15 generally holds less water than tank 21 in the first embodiment, this design eliminates the need to manually transfer water from an external separate purification tank to the storage area.

Referring now to FIGS. 4–8, a variety of features may be added to the above noted embodiments, as follows.

Figure 4:
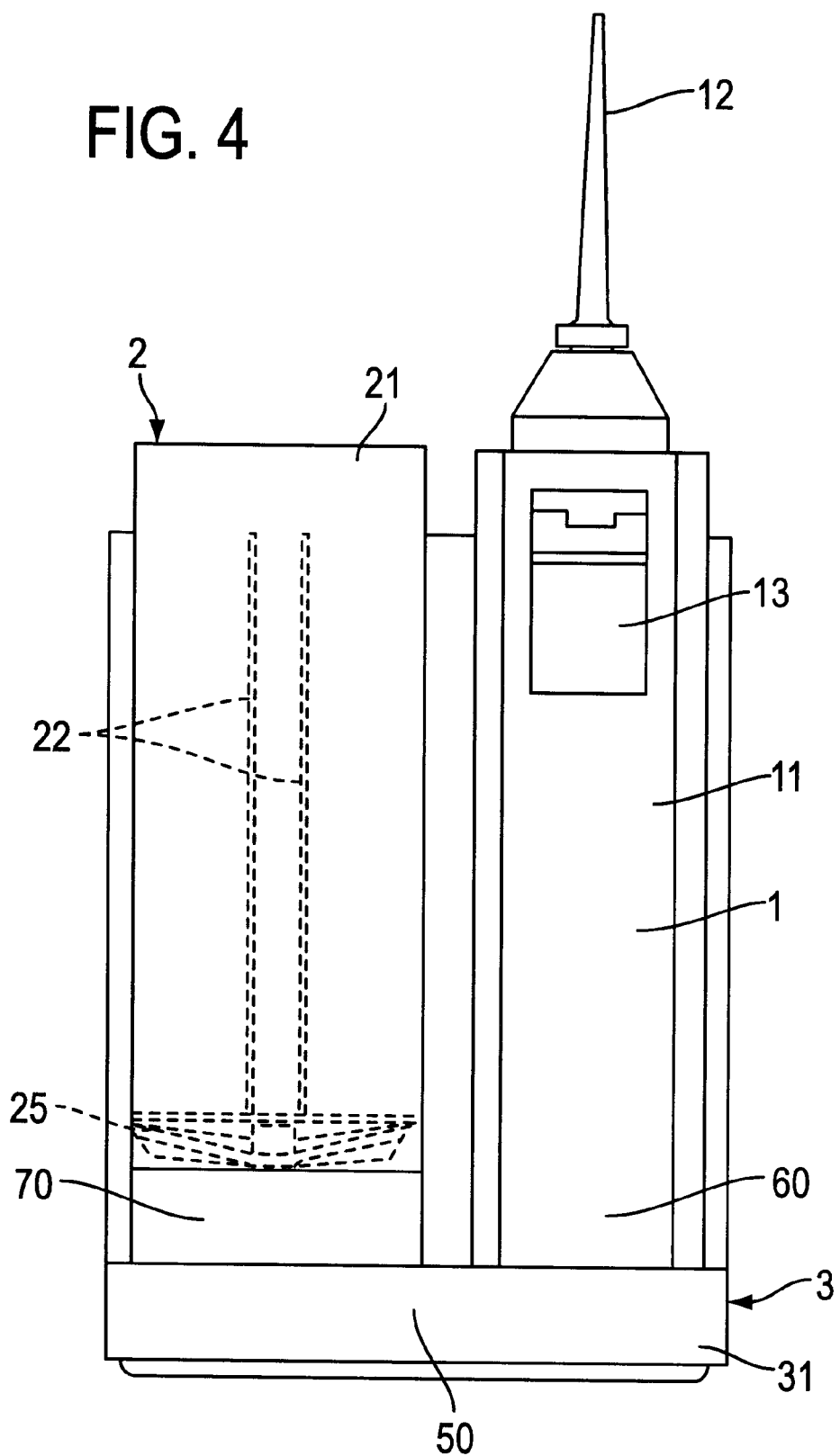
FIG. 4 is a front view of a water purification and dispensing device with a stirring element.

Referring now to FIG. 4, as is known in the art of electrolysis, water at top of purification tank 21 tends to have a lower PH than water at the bottom of the tank. A stirrer 25 is therefore placed at the bottom of purifier tank 21. When started, it forms vertical fluid currents in purifier 21, creating a solution with a homogenous PH. Since stirrer 25 would draw power away from electrodes 22 during a purification cycle (thereby slowing the process), activating stirrer 25 only after completion of the purification cycle is preferable (i.e., when voltage is not applied to electrodes 22).

Figure 5:
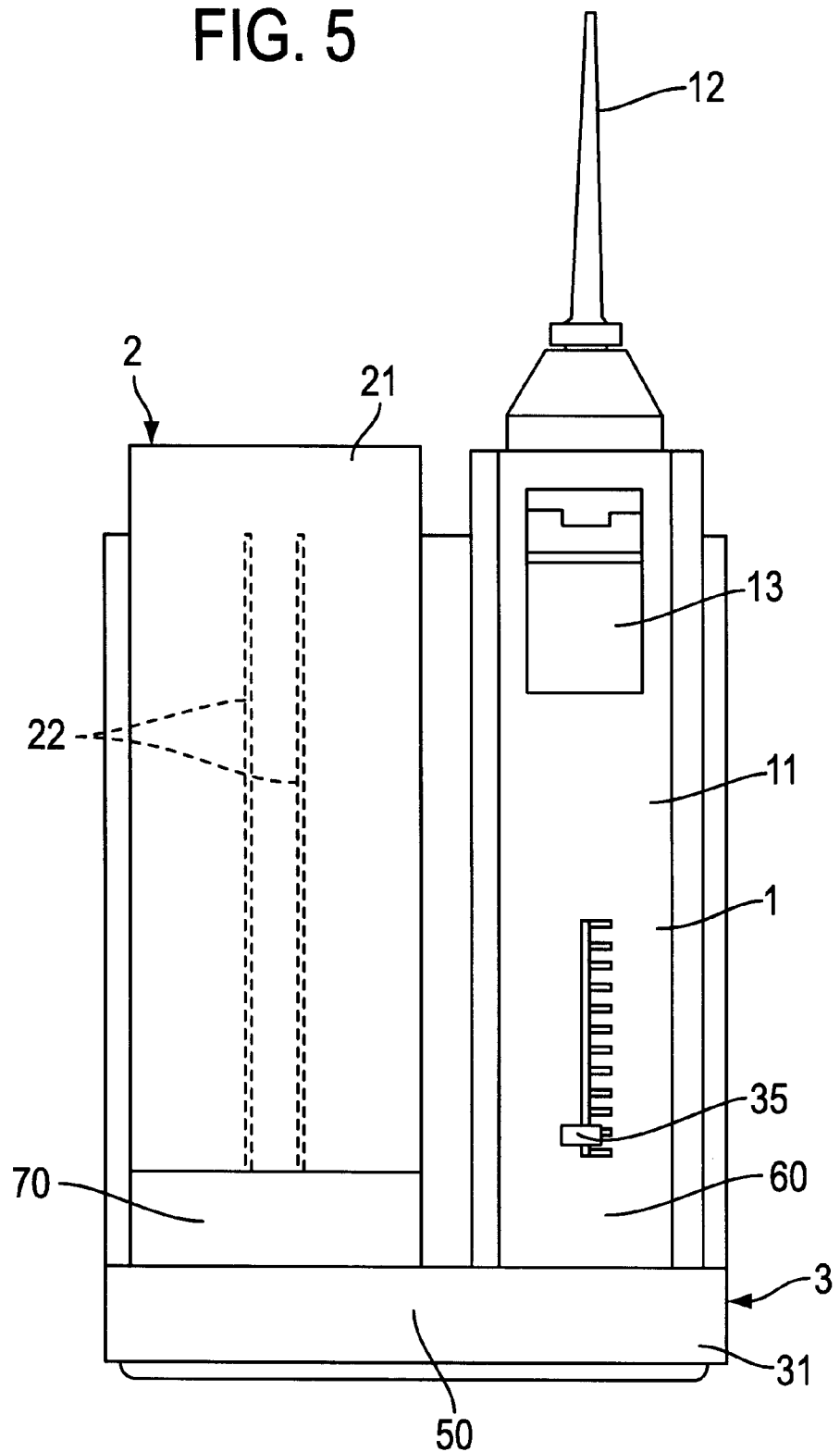
FIG. 5 is a front view of a water purification and dispensing device with a variable speed switch.
Figure 6:
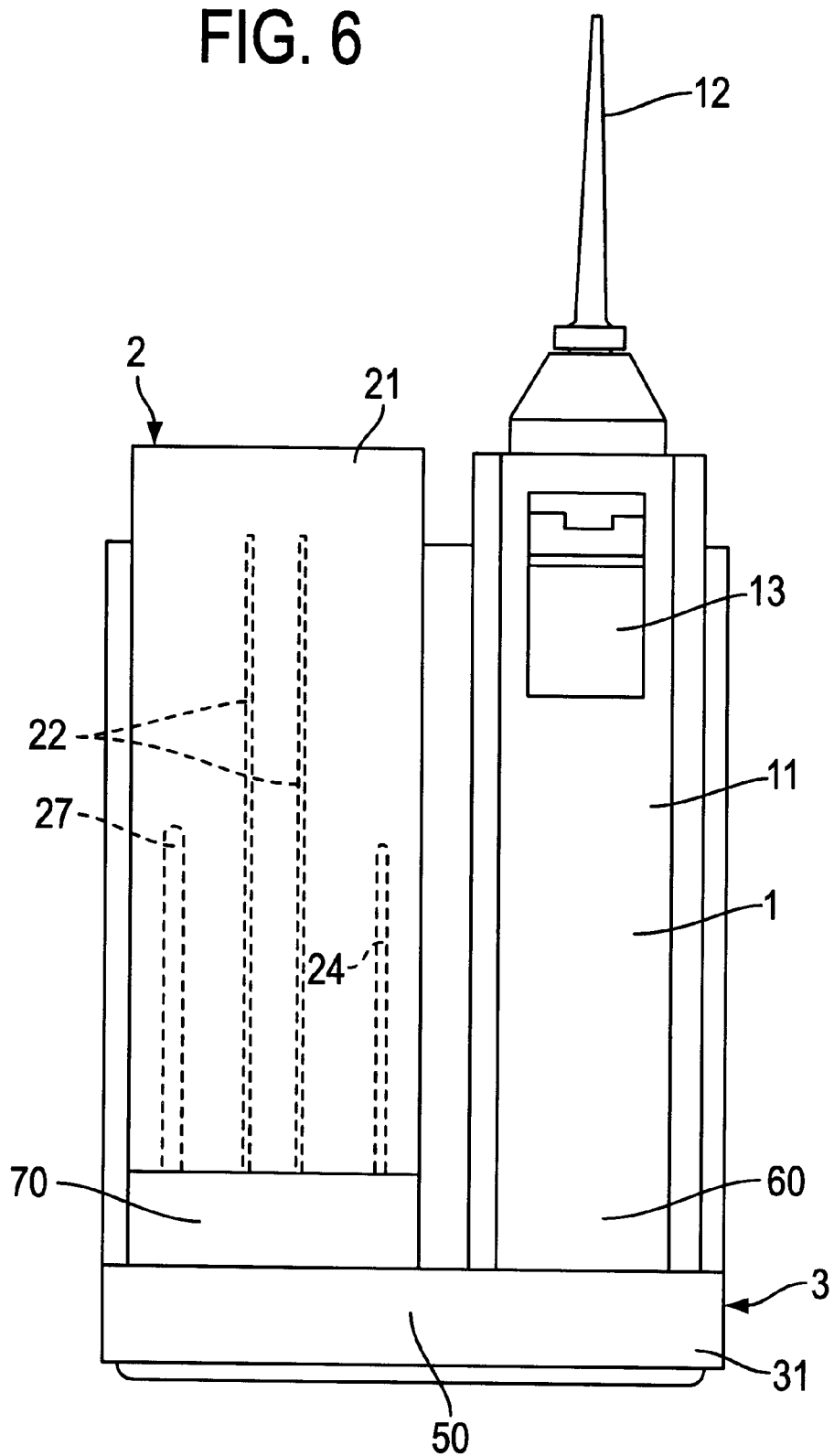
FIG. 6 is a front view of a water purification and dispensing device with temperature control elements.
Figure 7:
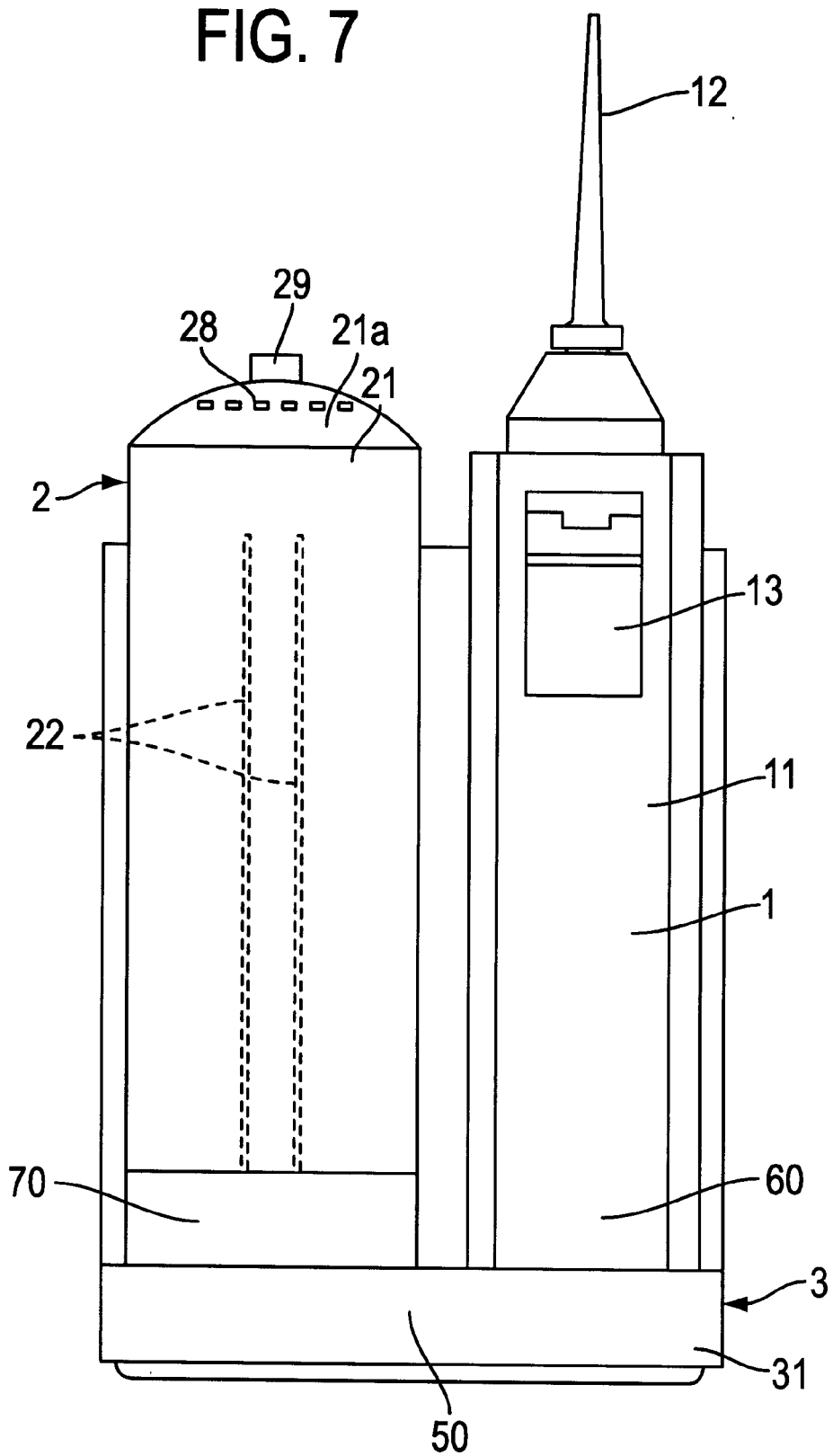
FIG. 7 is a front view of a water purification and dispensing device with a gas removing lid.

Referring now to FIG. 5, a variable switch 35 is provided to adjust the discharge pressure exerted by pump 14 during discharge of water through nozzle 12. This permits the use of high pressure to remove debris or bacteria on teeth, as well as a gentler mode to wash sensitive areas, such as eyes. The location and connection of switch 35 with switch 13, power receiving circuit 60, and pump 14 is believed well within the scope of the art, and thus a detailed circuit schematic is omitted.

In the above embodiments, the water is usually at room temperature. However, a user may be sensitive to cold water due to medical conditions, (e.g., tooth disease). The embodiment of FIG. 6 therefore adds a temperature sensor 24 and temperature adjusting element 27 to purification tank 21. If temperature element 27 is a heating element, based on the temperature read by sensor 24, the water temperature can be raised to a more comfortable level (e.g., body temperature). Similarly, if temperature element 27 is a cooling element (e.g., a Peltier device) the temperature of the water could be lowered.

For another feature of the present invention, it is commonly known that hydrogen and oxygen are byproducts of the electrolysis of water. To remove any potential safety hazard, in the embodiment shown in FIG. 7, purifying tank 21 is provided with a removable lid 21a having an opening 29 and a catalyst 28 (such as silver). Catalyst 28 absorbs hydrogen gas produced during electrolysis and discharges it through opening 29.

Figure 8:
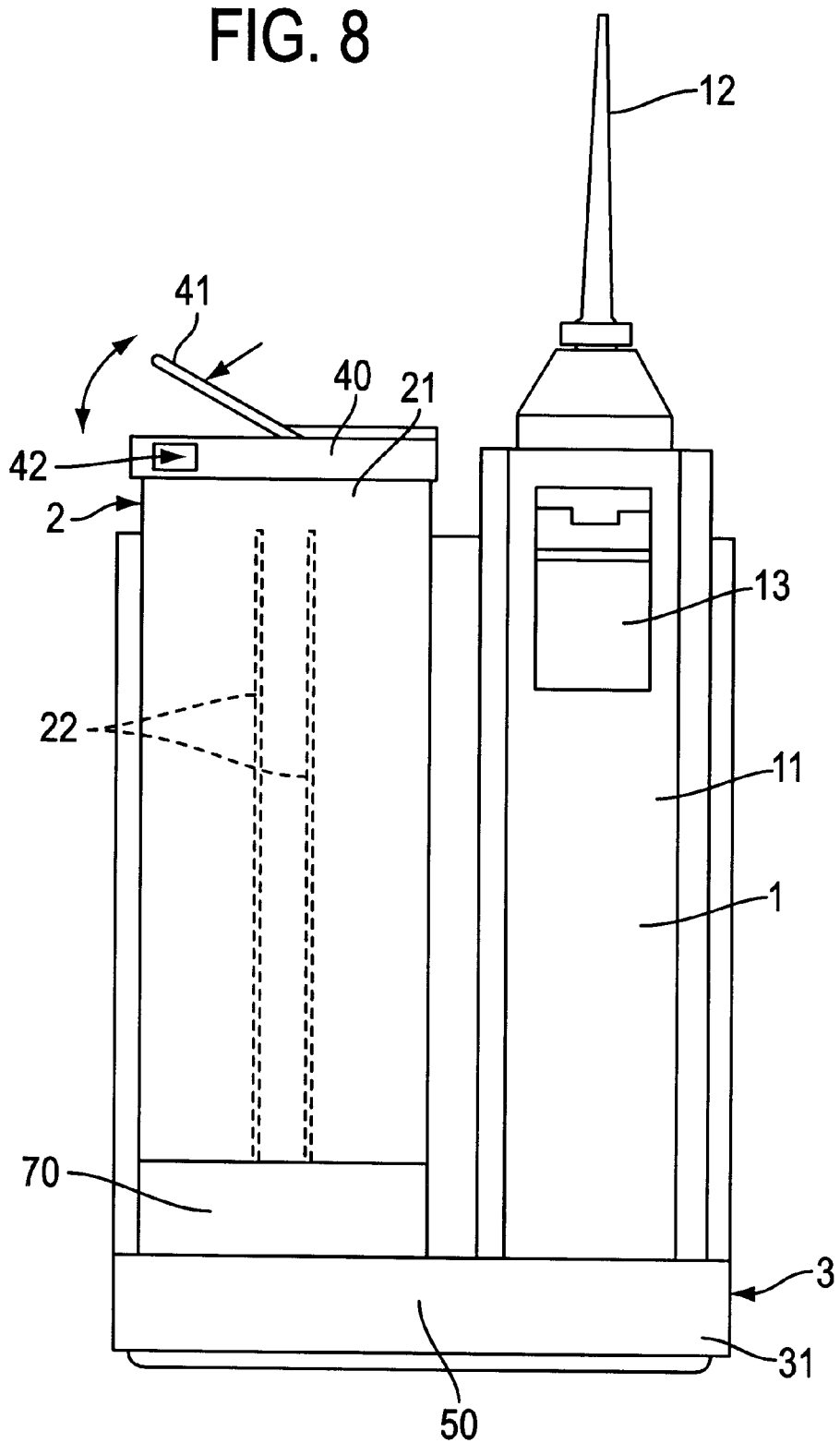
FIG. 8 is a front view of a water purification and dispensing device with a flexible lid.

In the embodiment of FIGS. 1a and 1b, purifying tank 21 has an open top to ease filling and emptying of the tank. However, this exposes electrodes 22 to the outside environment, which could cause a shock if a person touches electrodes 22 during the purification cycle. Accordingly, as shown in FIG. 8, a top 40 with flip lid 41 can be provided to the top of purifying tank 21, thereby preventing accidental contact with active electrodes. Optionally, an appropriate switch 42 may be used to cut power to electrodes 22 unless lid 41 is closed.

In FIGS. 4–8, each of the various features has been shown with the separate dispenser 1 and purification tank 2 of the embodiment shown in FIGS. 1a and 1b. However, these features may also be used with the integrated design of FIGS. 3a and 3b. Similarly, any combination of these features may be incorporated into a single device as needed.

The present invention also contemplates the use of various power supplying circuits and power receiving circuits, shown in FIGS. 9–14.

Figure 9:
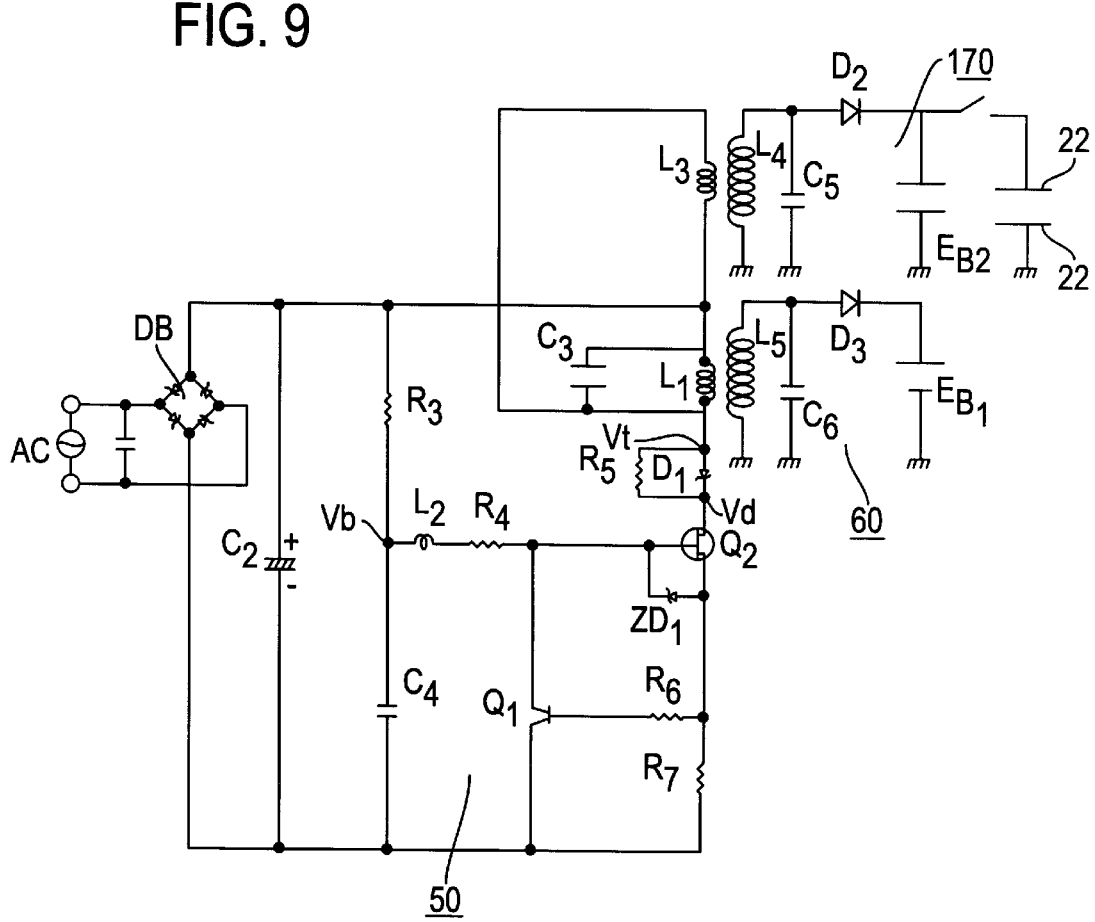
FIG. 9 is a schematic diagram of a second circuit for providing voltage to the electrodes.

Referring to FIG. 9, electrodes 22 may receive power through power receiving circuit 170. Circuit 170 differs from power receiving circuit 70 through the provision of a second rechargeable battery EB2, which connects to electrodes 22 through a switch. Electrodes 22 may thus be powered by battery EB2 rather than through the direct application of voltage as in power receiving circuit 70. This is particularly useful when an electrical outlet is either unavailable or not very close to the area in which purifier 2 is to be used.

Figure 9A:
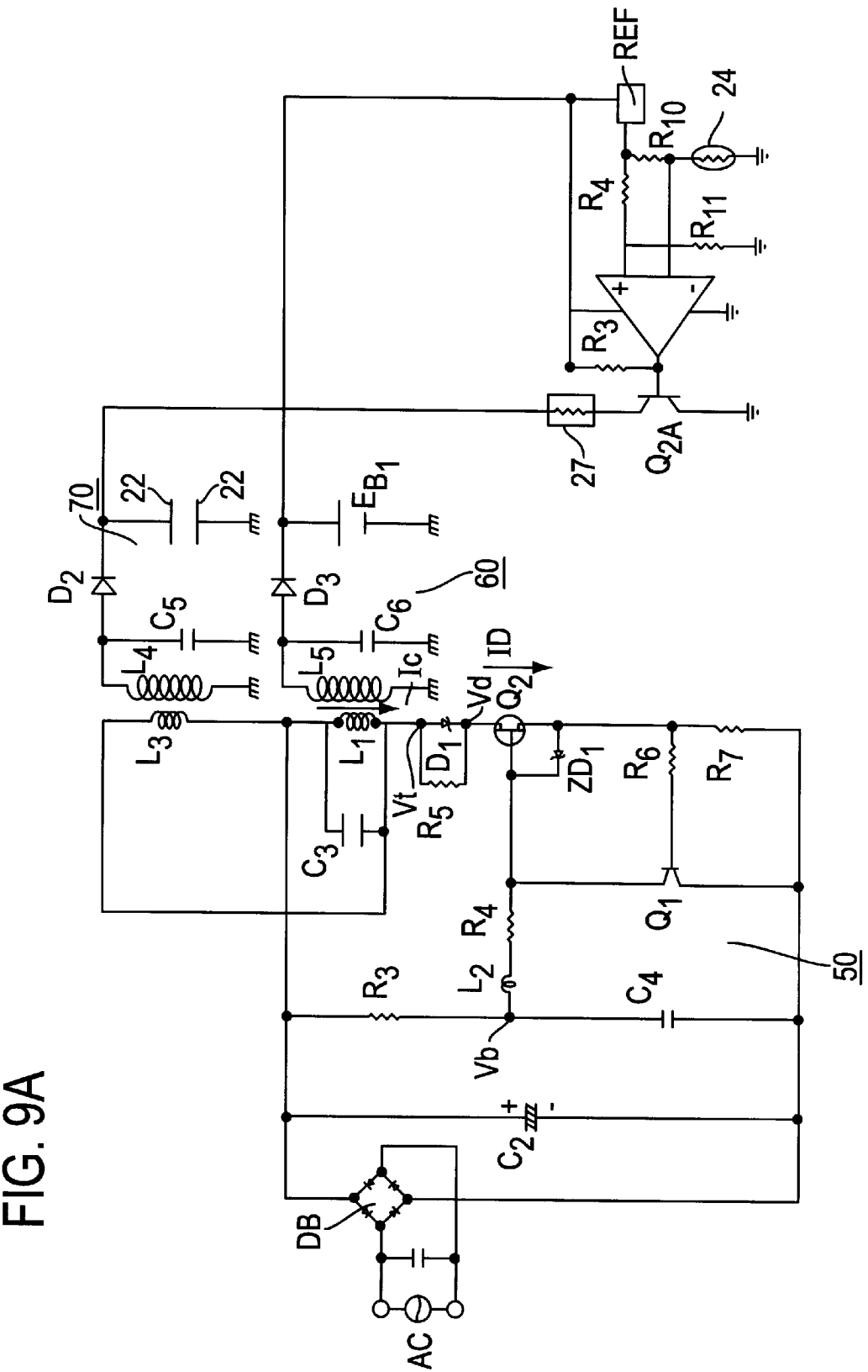
FIG. 9A is a schematic diagram of a circuit for powering temperature adjustment elements.

FIG. 9A shows an example of circuit for adjusting water temperature. A comparator receives a voltage ref based on the desired temperature, and the output of temperature sensing element 24. When a difference is detected, the comparator outputs a signal to turn transistor Q2A ON, supplying power to temperature adjusting element 27.

Figure 10:
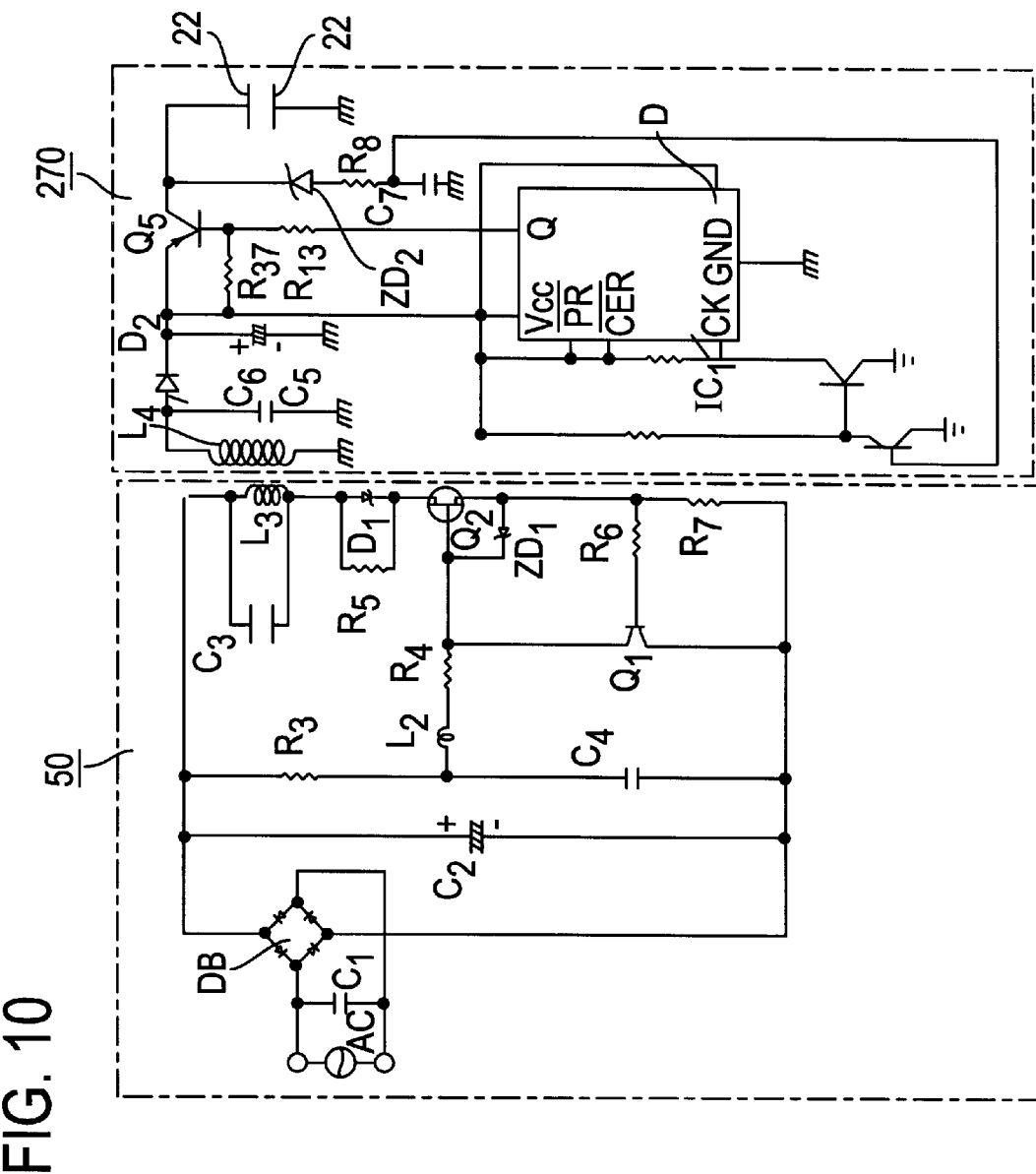
FIG. 10 is a schematic diagram of a third circuit for providing voltage to the electrodes.

Electrodes 22 may also be powered by a power receiving circuit 270 shown in FIG. 10. Circuit 270 cuts off the supply of power to electrodes 22 when the purifying tank 21 (or water storage area 15 for the integral embodiment) is empty, thereby avoiding the possibility of electric shock. In power supply 270, a transistor Q5 is disposed between diode D2 and electrodes 22. Transistor Q5 is turned ON and OFF by latch circuit IC1 through a Q terminal of latch circuit IC1. Electrodes 22 connect in parallel with the series circuit of capacitor C7, resistor R8, and zener diode ZD2.

When water is between electrodes 22, transistor Q2 is OFF and transistor Q3 is ON. Transistor Q5 is therefor ON, such that current flows between electrodes 22 in the normal manner. However, if the current path is interrupted due to a lack of water, then current flows through zener diode ZD2 (typically when the purifying tank is empty or with a small amount of water), and resistor R8 to charge capacitor C7. Transistor Q2 turns ON when the change of capacitor C7 exceeds the threshold voltage of transistor Q2, turning transistors Q3 and Q5 OFF, cutting power to electrodes 22. Thus, when current does not flow between electrodes 22 due to an absence of sufficient water in purifying tank 21, electrodes 22 are disconnected, thereby preventing any electric shock.

Figure 11:
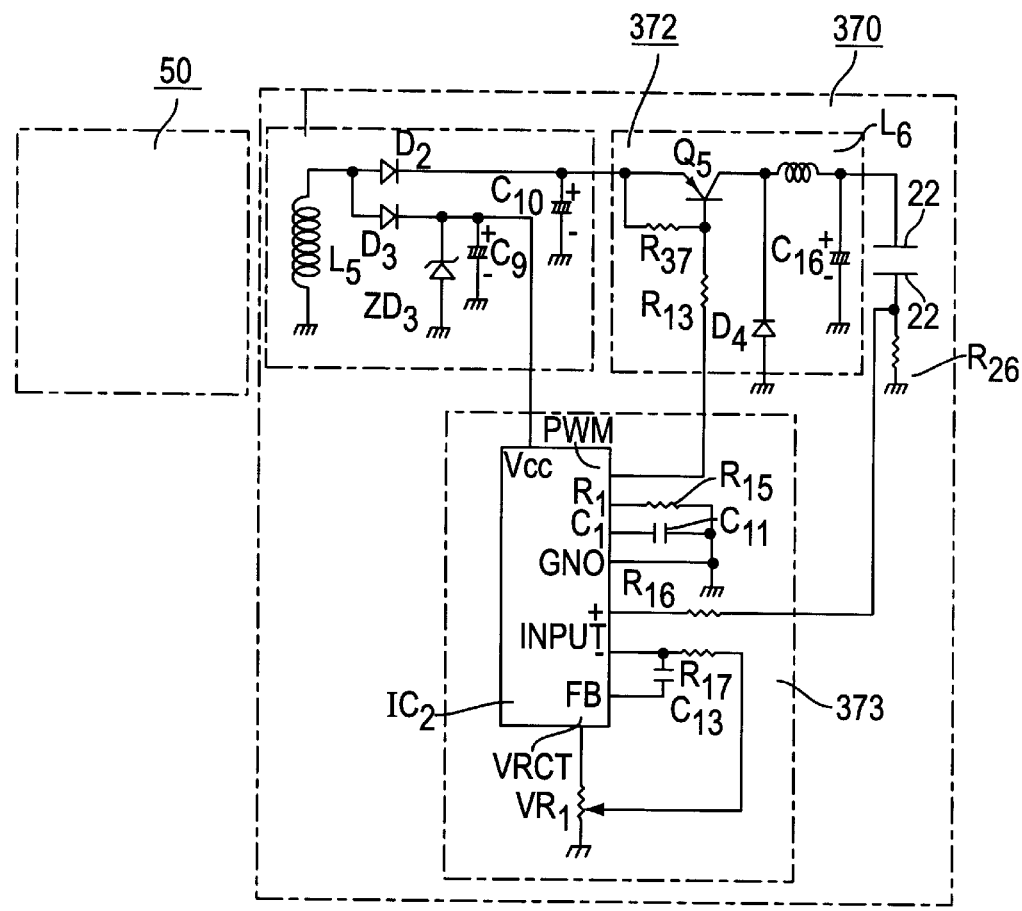
FIG. 11 is a schematic diagram of a fourth circuit for providing voltage to the electrodes.

Referring now to FIG. 11, a power receiving circuit 370 may be used to provide a constant current to electrodes 22 under control of a Pulse Width Modulator 373. In this embodiment, the current through electrodes 22 is detected by a resistor R26 in series with electrodes 22. A differential amplifier in a control circuit 1C2 compares the voltage of resistor R26 with a reference voltage (set by adjusting a variable resistor VR1). Control circuit IC2 compares the output of the differential amplifier with a triangular wave to output the pulse width modulated signal to the gate of transistor Q5. Control circuit IC2 receives power at its Vcc terminal from the DC voltage applied by inductor L5, diode D3, and capacitor C9.

In combination with the smoothing effect exerted by the combination of diode D4, inductor L6, and capacitor C16, the pulse width modulated signal applied to transistor Q5 maintains a substantially constant current to electrodes 22, regardless of load or voltage fluctuation in the circuit. In addition, adjusting variable resistor VR1 can change the current between electrodes 22 to a desired level.

In the above power receiving circuits, current flows in only one electrode 22 to the other. Because of this unidirectional current, one electrode experiences a great deal of erosion, which does not affect the other electrode. A power supply circuit 470 shown in FIG. 12 addresses this problem by reversing the direction of current flow during the purification cycle, thereby distributing the erosion evenly to both electrodes.

Power circuit 470 includes a switching circuit 474, and a control 475. Switching circuit 474 includes a bridge circuit formed by four transistors Q6–Q9, and a capacitor C10 connected to both input terminals of switching circuit 474. The bases of transistors Q6 and Q7 connect to the opposite side of the bridge through resistors R26a and R27. A control circuit IC3 of control 475 has a first output OUT1 connected with the base of transistor Q8 through a resistor R28, and a second output OUT2 connected with the base of transistor Q9 through a resistor R29. A time constant is set for circuit IC3 by capacitor C15 and resistors R21 and R22.

When power supply circuit 50 is turned on, voltage is provided to the Vcc terminal of circuit IC3 at the output of diode D7. Circuit IC3 outputs a HIGH signal at terminal OUT1, and a LOW signal at terminal OUT2. Transistors Q7 and Q8 turn ON, forming a current path in the direction of the arrow A between electrodes 22. When a predetermined time (preferably at the midpoint of a purification cycle) based on the time constant elapses, OUT1 changes to LOW, while OUT2 changes to HIGH. Transistors Q7 and Q8 turn OFF and transistors Q6 and Q9 turn ON, forming a current path between electrodes 22 in a direction opposite arrow A. When the timer period elapses, OUT2 returns to LOW, turning transistors Q6 and Q9 OFF. This stops the supply of current to electrodes 22, ending the purification cycle.

Figure 12:
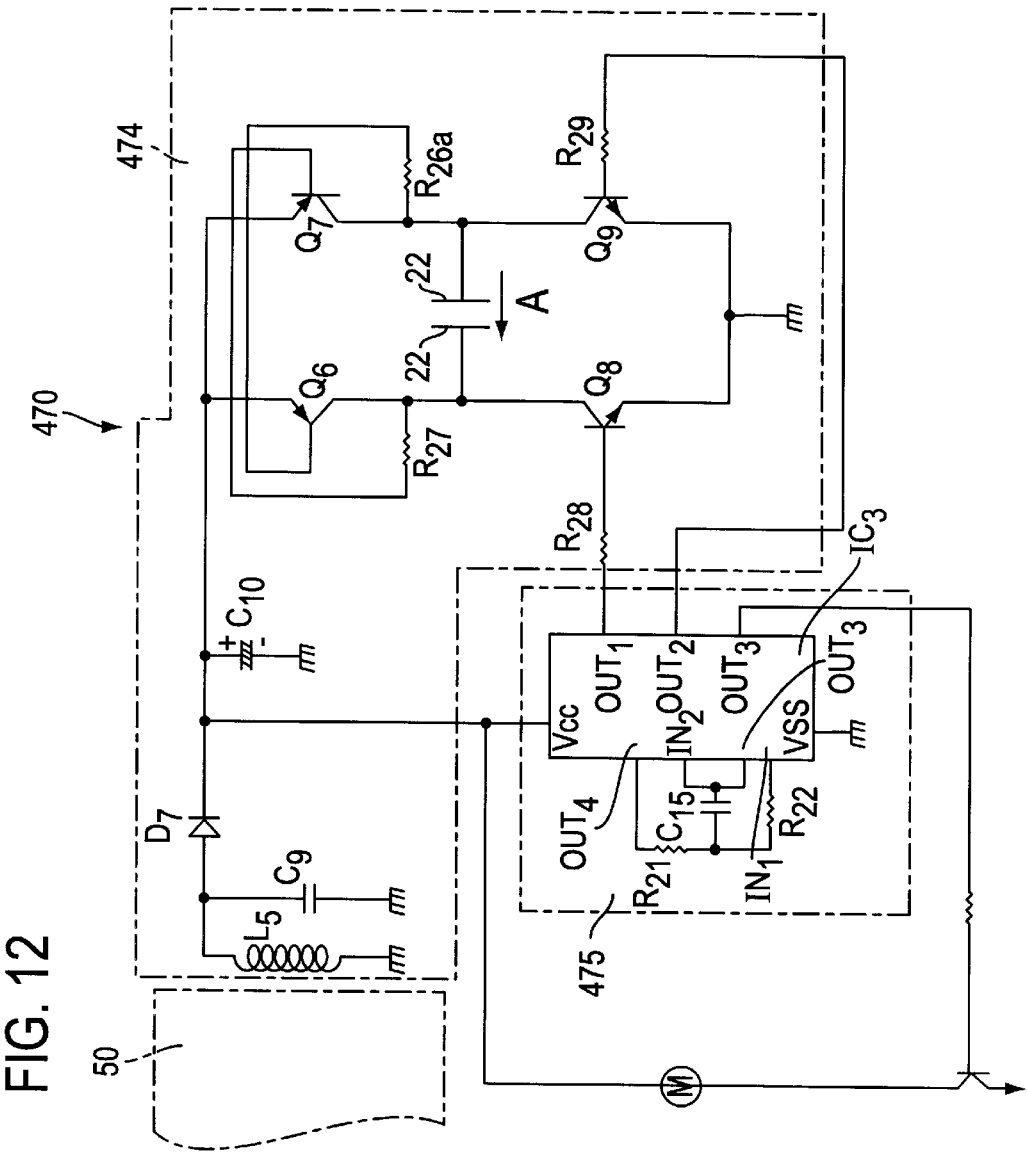
FIG. 12 is a schematic diagram of a fifth circuit for providing voltage to the electrodes.

FIG. 12 also shows an example of how a motor M for stirrer 25 is operated. An output OUT3 of IC circuit IC3 goes HIGH when OUT2 goes LOW. This turns the transistor connected to OUT3 ON, thereby passing current to motor M to rotate stirrer 25.

Power switching circuit 474 thus changes the direction of current flow between electrodes 22 to distribute the erosion evenly to both electrodes 22. Current flow preferably changes at the midpoint of the purification cycle, as any further switching of the current flow accelerates the erosion due to rush currents. In addition, if circuit IC3 gradually changes the state of OUT1 and OUT2, i.e., if the current between electrodes 22 is gradually decreased before the direction change and gradually increased after the direction changes, this further reduces rush currents and the erosion caused thereby.

Figure 13:
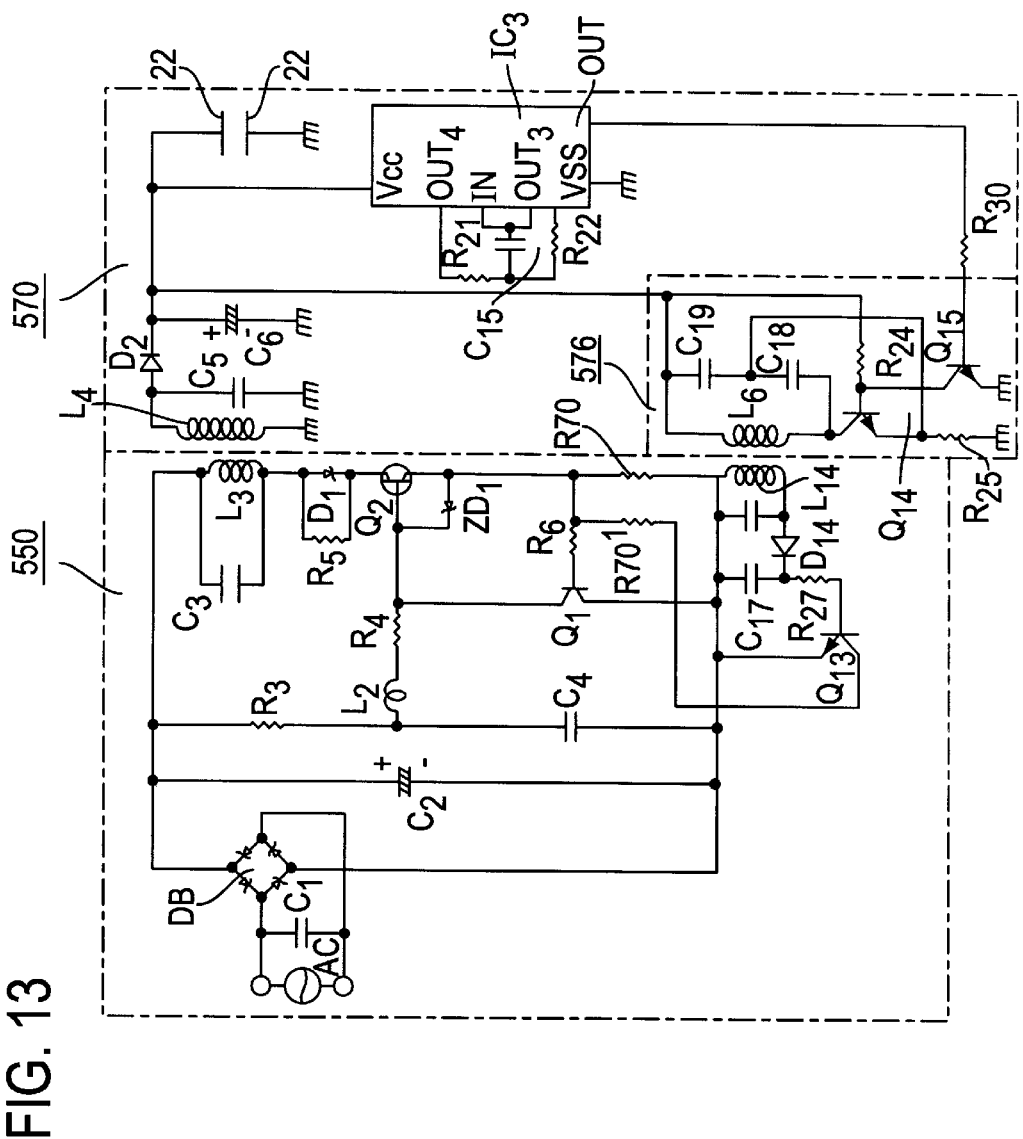
FIG. 13 is a schematic diagram of a sixth circuit for providing voltage to the electrodes.

The above embodiments consume electricity regardless of whether dispenser 1 or purifier 2 is mounted on base 3, and therefore waste electricity when these items are not mounted on base 3. To reduce such waste, a power receiving circuit 570 and power supply circuit 550 is shown in FIG. 13.

Power receiving circuit 570 has a timing control circuit IC3 with a time constant set by capacitor C15 and resistors R21 and R22. Source control circuit 576 receives an output of circuit IC3 through a resistor R30, as well as an oscillation signal from the circuit formed by inductor L4 and capacitors C5 and C6. Inductor L6, capacitors C18 and C19, resistors R24 and R25, and transistor Q14 of source control circuit 576 form a Collpits oscillator, which operates in a known manner.

When purifier 2 is not mounted on base 3, resistor R70 of power source circuit 550 is the only current path for current IL. Resistor R70 has a relatively large resistance, such that current flow is minimal during this low power consumption mode.

When purifier 2 is mounted on base 3, the current through inductor L3 is sufficient to power the Vcc terminal of control circuit IC3. Control circuit IC3 initiates a timer, during which time its OUT terminal is LOW, turning transistor Q15 OFF and transistor Q14 ON. The resultant oscillating current passing through inductor L6 produces a corresponding current in inductor L14 through mutual inductance. Transistor Q13 turns ON, placing resistor R70 and R70' in parallel.

Resistor R70' has a lower resistance than resistor R70, such that the resultant combined parallel resistance (R70∥R70') is much less than that of resistor R70. Since the voltage remains constant, the current flow through resistors R70 and R70', as well as inductor L3, substantially increases. This in turn generates higher current to electrodes 22 through mutual inductance between inductor L3 and inductor L4 of power receiving circuit 570.

When the time set by timer circuit IC3 elapses, the OUT terminal of circuit IC3 changes to HIGH, turning transistor Q5 ON and Q14 OFF. Transistor Q13 turns OFF responsive to the loss of current through inductors L6 and L 14, removing the current path through resistor R70'. The circuit thus returns to a lower power consumption mode.

In the above embodiment, power receiving circuit 60 is identical to that of FIG. 2. Inductor L1 is thus omitted from the schematic of FIG. 13 for ease of reference, although it remains in parallel with inductor L3 as in FIG. 2.

Figure 14:
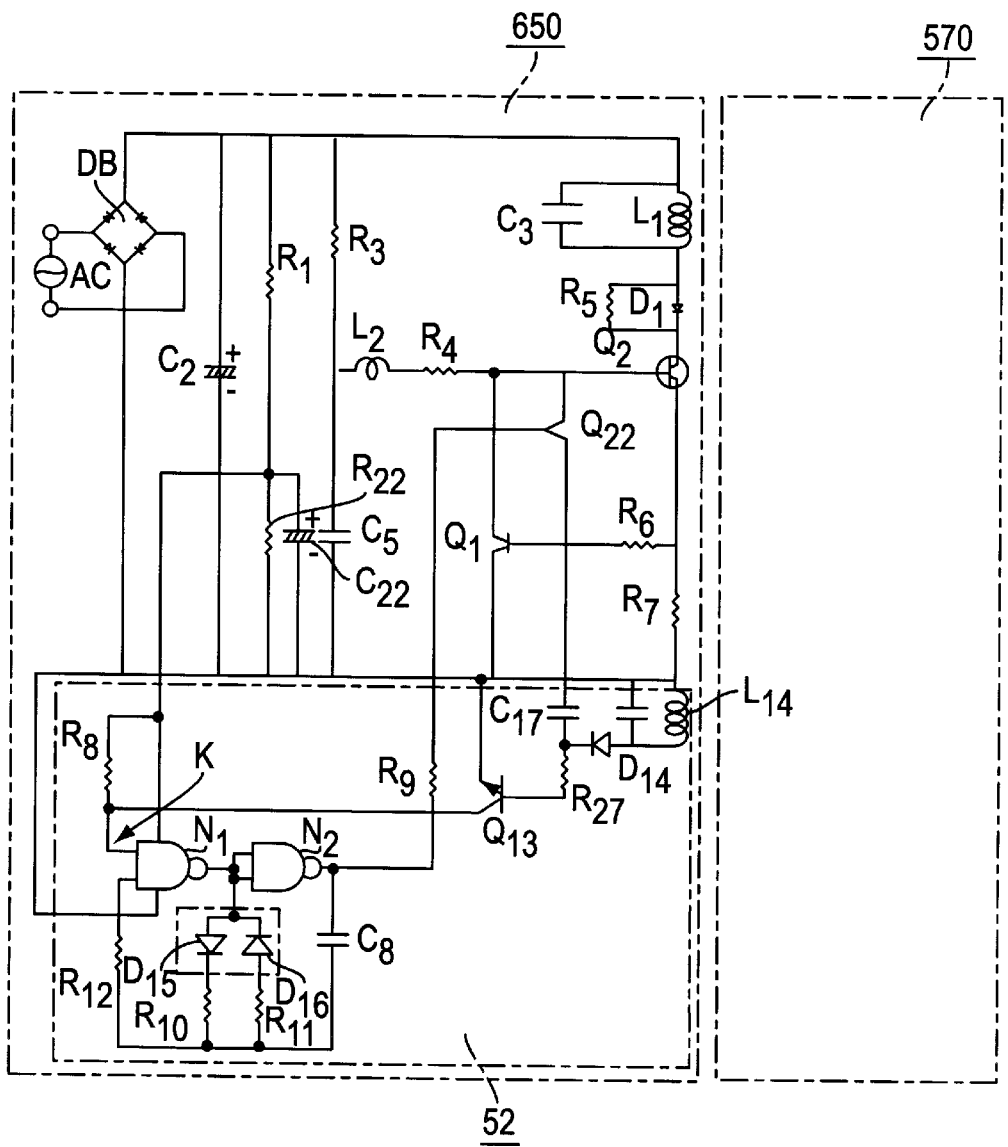
FIG. 14 is a schematic diagram of a seventh circuit for providing voltage to the electrodes.

A variant of the above embodiment uses power receiving circuit 570 with a power supply circuit 650 as shown in FIG. 14. In this embodiment, resistor R70' of power supplying circuit 550 is replaced with a transistor Q22 having its source connected with the gate of transistor Q2, and its gate connected to a blocking oscillation control circuit 52. Control circuit 52 includes NAND gates N1 and N2, resistors R8–R12, capacitor C8 and diodes D15 and D16.

When the unit to be powered (washer 1 or purifier 2) is not on base 3, the input to NAND gate N1 at point K is HIGH, producing an oscillating output at NAND gate N2. This output charges capacitor C8, keeping transistor Q22 ON for long periods and reducing the period during which Q2 is ON. When the unit to be powered is placed on base 3, transistor Q13 turns ON, changing point K to LOW and the output of NAND gate N2 to LOW. Transistor Q22 turns OFF, allowing Q2 to operate in its normal manner.

It is noted that the above described circuits of FIGS. 9–14 may be used in either the separate unit embodiment of FIGS. 1a and 1b, or the integral embodiment of FIGS. 3a and 3b.

While the invention has been described with reference to several exemplary embodiments, it is understood that the words which have been used herein are words of description and illustration, rather than words of limitations. Changes may be made, within the purview of the pending claims, as without effecting the scope and spirit of the invention and its aspects. While the invention has been described here with reference to particular means, materials and embodiments, the invention is not intended to be limited to the particular disclosed herein; rather, the invention extends to all functionally equivalent structures, methods and uses, such at all within the scope of the appended claims.

By way of non-limiting example, several features of the present invention, including stirrer 25, variable speed switch 35, temperature sensor 24, temperature adjusting element 27, lid 21a, and top 40, are shown and discussed with reference to the embodiment of FIGS. 1a and 1b. However, these features may of course be used in the integral embodiment of FIGS. 3a and 3b. Similarly, the various power supply circuits and power receiving circuits can be used for the separate unit embodiment of FIGS. 1a and 1b and the integral unit embodiment of FIGS. 3a and 3b.

In another example, although variable speed switch 35 is shown as a scale, a knob or other switch design could be used. Further, switch 35 could adjust the speed linearly (e.g., through a potentiometer) or step-wise (e.g., any number of preset speeds). Still further, switch 13 and switch 35 could be combined into a single switch.

In yet another example, although the timer circuit IC3 and control circuit 574 of FIG. 13 are in power supply circuit 570 for purifier 2, these elements could alternatively be placed in the power supply circuit for dispenser 1.

In still yet another example, although the present invention has been described with reference to purifying and dispersing water, any fluid may be used.

In still yet another example, various microchips for control circuits IC1, IC2 and IC3 may be used. At present, IC1 is preferably a Toshiba TC7WH74FU, IC2 is preferably a Rome 9700AF PWM control microchip, while IC3 is preferably a Motorola MC 14521 of the CMOS digital 4000 series. IC1 is a non-production chip which can be easily manufactured by one of ordinary skill based on the requirements of the associated circuit as described herein.

The present invention is related to Japanese Patent Application 8-314,364, filed on Nov. 26, 1996, the disclosure of which is expressly incorporated herein by reference in its entirety.

What is claimed is:

1. A device for purifying and dispensing a fluid, comprising:
   a dispenser including a fluid storage area, a pump which pumps fluid from said fluid storage area, and a first power receiving circuit having a first rechargeable battery for powering said pump;
   a purifying tank including a fluid purification area having a pair of electrodes and a second power receiving circuit connected to said pair of electrodes;
   said first and second power receiving circuits including at least first and second inductors, respectively;
   a base having a power supply circuit including at least third and fourth inductors, said dispenser and said purifying tank being removably mounted on said base such that said first and third inductors and said second and fourth inductors are in sufficient proximity to each other to form mutual inductance therebetween when said dispenser and said purification tank are mounted on said base, respectively, such that current passing through said third inductor induces current in said first inductor, and current passing through said fourth inductor induces current in said second inductor.

2. The device of claim 1, further comprising a variable switch for changing an operating speed of said pump.

3. The device of claim 1, further comprising a stirrer which stirs fluid in said purifying tank.

4. The device of claim 3, wherein said stirrer is positioned at a bottom of said purifying tank.

5. The device of claim 3, wherein said stirrer is inactive when voltage is applied to said pair of electrodes.

6. The device of claim 3, further comprising a temperature adjusting element associated with said purifying tank to at least one of increase and decrease a temperature of a fluid in said purifying tank.

7. The device of claim 1, wherein said second power receiving circuit further comprises a timer circuit which controls the period of time that voltage is applied to said pair of electrodes.

8. The device of claim 1, wherein said second power receiving circuit further comprises a constant current circuit for providing a constant current to said pair of electrodes.

9. The device of claim 8, further comprising a variable switch which adjusts an amount of current produced by said constant current circuit.

10. The device of claim 1, wherein said second power receiving circuit further comprises a switching circuit which changes a direction of current flow between said pair of electrodes.

11. The device of claim 10, wherein said switching circuit only changes said direction of current flow once during a purification cycle.

12. The device of claim 10, wherein said switching circuit gradually decreases the current before changing said direction of current flow, and then gradually increases the current after changing said direction of current flow.

13. The device of claim 1, wherein said first power receiving circuit receives power through mutual inductance between said first and third inductors to apply voltage to charge said first rechargeable battery.

14. The device of claim 1, wherein said second power receiving circuit receives power through mutual inductance between said second and fourth inductors to apply voltage to said pair of electrodes.

15. The device of claim 1, wherein said second power receiving circuit receives power through mutual inductance between said second and fourth inductors to charge a second rechargeable battery in said second power circuit, said second battery applying voltage to said pair of electrodes through a switch.

16. The device of claim 1, wherein said first power source further comprises a mechanism which prevents the application of voltage to said pair of electrodes when said purifying tank does not have enough fluid to create a current path between said electrodes.

17. The device of claim 1, wherein said purifying tank has a lid with a catalyst which absorbs gases produced during purification of said fluid, and an opening to expel said gases.

18. The device of claim 1, wherein said purification tank has a pivoted lid and a switch associated with said lid which prevents current from flowing to said electrodes when said lid is open.

19. The device of claim 1, said power supplying circuit further comprising a circuit which minimizes a current flow through said first and second inductors when said purification tank is not mounted on said base, and which increases said current flow through said first and second inductors when said purification tank is mounted on said base.

20. A device for purifying and dispensing a fluid, comprising:
   a dispenser including a fluid purification area, a pump which pumps fluid from said fluid purification area, and a first power receiving circuit having a first rechargeable battery for powering said pump;
   said fluid purification area having a pair of electrodes and a second power receiving circuit connected to said pair of electrodes;
   said first and second power receiving circuits including at least first and second inductors, respectively;
   a base having a power supply circuit including at least third and fourth inductors, said dispenser being removably mounted on said base such that said first and third inductors and second and fourth inductors are in sufficient proximity to each other to form mutual inductance therebetween when said dispenser is mounted on said base, such that said current passing through said third inductor induces current in said first inductor, and current passing through said fourth inductor induces current in said second inductor.

21. The device of claim 20, further comprising a variable switch for changing an operating speed of said pump.

22. The device of claim 20, further comprising a stirrer which stirs fluid in said purifying tank.

23. The device of claim 22, wherein said stirrer is positioned at a bottom of said purifying tank.

24. The device of claim 22, wherein said stirrer is inactive when voltage is applied to said pair of electrodes.

25. The device of claim 22, further comprising a temperature adjusting element associated with said purifying tank to at least one of increase and decrease a temperature of a fluid in said purifying tank.

26. The device of claim 20, wherein said second power receiving circuit further comprises a timer circuit which controls the period of time that voltage is applied to said pair of electrodes.

27. The device of claim 20, wherein said second power receiving circuit further comprises a constant current circuit for providing a constant current to said pair of electrodes.

28. The device of claim 27, further comprising a variable switch which adjusts an amount of current produced by said constant current circuit.

29. The device of claim 20, wherein said second power receiving circuit further comprises a switching circuit for changing a direction of current flow between said pair of electrodes.

30. The device of claim 29, wherein said switching circuit only changes said direction of current flow once during a purification cycle.

31. The device of claim 29, wherein said switching circuit gradually decreases the current before changing said direction of current flow, and then gradually increases the current after changing said direction of current flow.

32. The device of claim 20, wherein said first power receiving circuit receives power through mutual inductance between said first and third inductors to apply voltage to charge said first rechargeable battery.

33. The device of claim 20, wherein said second power receiving circuit receives power through mutual inductance between said second and fourth inductors to apply voltage to said pair of electrodes.

34. The device of claim 20, wherein said second power receiving circuit receives power through mutual inductance between said second and fourth inductors to charge a second rechargeable battery in said second power circuit, said second battery applying voltage to said pair of electrodes through a switch.

35. The device of claim 20, wherein said first power source further comprises a mechanism which prevents the application of voltage to said pair of electrodes when said purifying tank does not have enough fluid to create a current path between said electrodes.

36. The device of claim 20, wherein said purifying tank has a lid with a catalyst which absorbs gases produced during purification of said fluid, and an opening to expel said gases.

37. The device of claim 20, wherein said purification tank has a pivoted lid and a switch associated with said lid which prevents current from flowing to said electrodes when said lid is open.

38. The device of claim 20, said power supplying circuit further comprising a circuit which minimizes a current flow through said first and second inductors when said purification tank is not mounted on said base, and which increases said current flow through said first and second inductors when said purification tank is mounted on said base.

* * * * *